United States Patent [19]

Langer

[11] 4,440,172
[45] Apr. 3, 1984

[54] APPARATUS FOR COMBINING PACING AND CARDIOVERTING FUNCTIONS IN A SINGLE IMPLANTED DEVICE

[75] Inventor: Alois A. Langer, Pittsburgh, Pa.

[73] Assignee: Mieczyslaw Mirowski, Owings Mills, Md.

[21] Appl. No.: 215,520

[22] Filed: Dec. 11, 1980

Related U.S. Application Data

[63] Continuation-in-part of Ser. No. 193,027, Oct. 2, 1980, abandoned.

[51] Int. Cl.$^3$ ............................................. A61N 1/36
[52] U.S. Cl. ........................ 128/419 D; 128/419 PG; 128/908
[58] Field of Search ............ 128/419 PG, 419 D, 696, 128/697, 902, 908

[56] References Cited

U.S. PATENT DOCUMENTS

| | | | |
|---|---|---|---|
| 3,513,850 | 5/1970 | Weber | 128/419 D |
| 3,533,003 | 10/1970 | Plaszczywski et al. | 128/902 |
| 3,547,108 | 12/1970 | Seiffert | 128/419 D |
| 3,614,955 | 10/1971 | Mirowski et al. | 128/419 D |
| 4,038,990 | 8/1977 | Thompson | 128/419 PG |
| 4,164,215 | 8/1979 | Finlayson et al. | 128/419 D |
| 4,320,763 | 3/1982 | Money | 128/908 |

Primary Examiner—William E. Kamm
Attorney, Agent, or Firm—Fleit, Jacobson, Cohn & Price

[57] ABSTRACT

The invention relates to an apparatus for combining pacing and cardioverting functions in a single implanted device, circuitry being provided not only to interface the defibrillator to the ECG amplifier and other elements of the device, but also to provide protection of the ECG amplifier from the defibrillator output pulses, from loading by the defibrillator itself, and from overloading by externally generated defibrillator pulses. A specific embodiment of the invention combines a defibrillator, a pacer and an ECG amplifier in a single implanted device utilizing two terminal-electrode lead combinations for connection to the patient, while further embodiments employ three and four terminal-electrode lead combinations. The invention employs a high-frequency transformer coupling technique for pacing, or, alternatively, high-frequency transformer coupling with modulation-demodulation. Moreover, in accordance with the invention, overloading of the ECG amplifier is prevented by provision of (in one embodiment) series-connected and oppositely oriented zener diodes, and (in a second embodiment) parallel-connected diodes in series with a blocking capacitor for blocking DC voltage.

45 Claims, 7 Drawing Figures

APPARATUS FOR COMBINING PACING AND CARDIOVERTING FUNCTIONS IN A SINGLE IMPLANTED DEVICE

REFERENCE TO RELATED APPLICATION

This is a Continuation-In-Part of copending application, U.S. Ser. No. 193,027, filed on Oct. 2, 1980, and assigned to the assignee of the present application.

BACKGROUND OF THE INVENTION

1. Field of the Invention

The present invention relates to an apparatus for combining pacing and cardioverting functions in a single implanted device, and more particularly to interface and protection circuitry for use in conjunction with defibrillator systems or combined defibrillator-pacer systems.

2. Description of the Prior Art

In recent years, substantial progress has been made in the development of defibrillation techniques for providing an effective medical response to various heart disorders or arrhythmias. The types of contemplated disorders or arrhythmias are typically treated by use of defibrillators and/or pacers, and typical arrangements also employ electrocardiograph (ECG) amplifiers for sensing heart activity and providing amplified electrical signals corresponding thereto and/or for synchronizing the employed technique with the heart activity.

A problem arises in the use of defibrillation circuitry in conjunction with ECG amplifiers, in that the sensitive circuitry of the ECG amplifier must be protected from defibrillation pulses. In addition, loading of the ECG amplifier by the relatively low impedance of the defibrillator output must be prevented. Moreover, it is desirable to protect the implanted defibrillator from external defibrillator pulses.

When a pacer is to be employed with an implantable defibrillator, it is similarly desirable to protect the pacer from the defibrillator pulses. Moreover, in certain other arrangements, it is desirable to provide additional protection and interface of the pacer circuitry, as will be discussed below.

SUMMARY OF INVENTION

According to the present invention, there is provided an apparatus for combining pacing and cardioverting functions in a single implanted device, circuitry being provided not only to interface the defibrillator to the ECG amplifier and other elements of the device, but also to provide protection of the ECG amplifier from the defibrillator output pulses. One embodiment for the protection circuitry, in accordance with the present invention, provides a high-resistance resistor between the defibrillation circuit and the ECG amplifier, with series-connected, oppositely oriented zener diodes being provided between the resistor and the ECG amplifier, on the one hand, and ground, on the other hand. Another embodiment for the prevention circuitry provides the high-resistance resistor, together with a DC-blocking capacitor between the defibrillator circuit and the ECG amplifier, with back-to-back diodes being provided between the blocking capacitor and the ECG amplifier, on the one hand, and ground, on the other hand.

In accordance with a further feature of the present invention, circuitry has been developed to provide protection of the implanted defibrillator from external defibrillator pulses. That is to say, the present invention is directed to providing protection circuitry for an implantable defibrillator.

The present invention is further directed to providing interface and protection circuitry for combined defibrillator-pacer systems, so that pacers are protected from the harmful effects of defibrillator pulses, and are as well isolated from other harmful elements of the system, as will be discussed in more detail below.

Therefore, it is an object of the present invention to provide an apparatus for combining pacing and cardioverting functions in a single implanted device.

It is a further object of the present invention to provide an apparatus for protecting ECG amplifier circuitry from defibrillator output pulses.

It is a further object of the present invention to provide an apparatus for preventing loading of the ECG amplifier by the defibrillator output.

It is a further object of the present invention to provide an apparatus containing circuitry for blocking DC signals from reaching the ECG amplifier and associated circuitry.

It is a further object of the present invention to protect an implantable defibrillator from external defibrillator pulses.

It is an additional object of the present invention to provide interface and protection circuitry for combined defibrillator-pace systems.

It is an additional object of the present invention to protect pacer circuitry from harmful effects of defibrillator output pulses.

It is an additional object of the present invention to provide isolation of an implanted pacer from other harmful effects of implantable defibrillator systems.

It is an additional object of the present invention to provide interface and protection circuitry wherein defibrillator pulses and pacing pulses are transmitted over the same lead pair.

It is an additional object of the present invention to provide an SCR triggering scheme which prevents SCR leakage current from reaching the patient during capacitor charging.

The above and other objects that will hereinafter appear, and the nature of the invention, will be more clearly understood by reference to the following description, the appended claims, and the accompanying drawings.

DETAILED DESCRIPTION

The first aspect of the present invention will now more fully be described with reference to FIG. 1A, which is a schematic representation of the present invention as employed in an implanted defibrillator system to protect the ECG amplifier from defibrillation pulses, and to prevent loading of the ECG amplifier by the defibrillator output circuit.

Figures 1A, 1C:
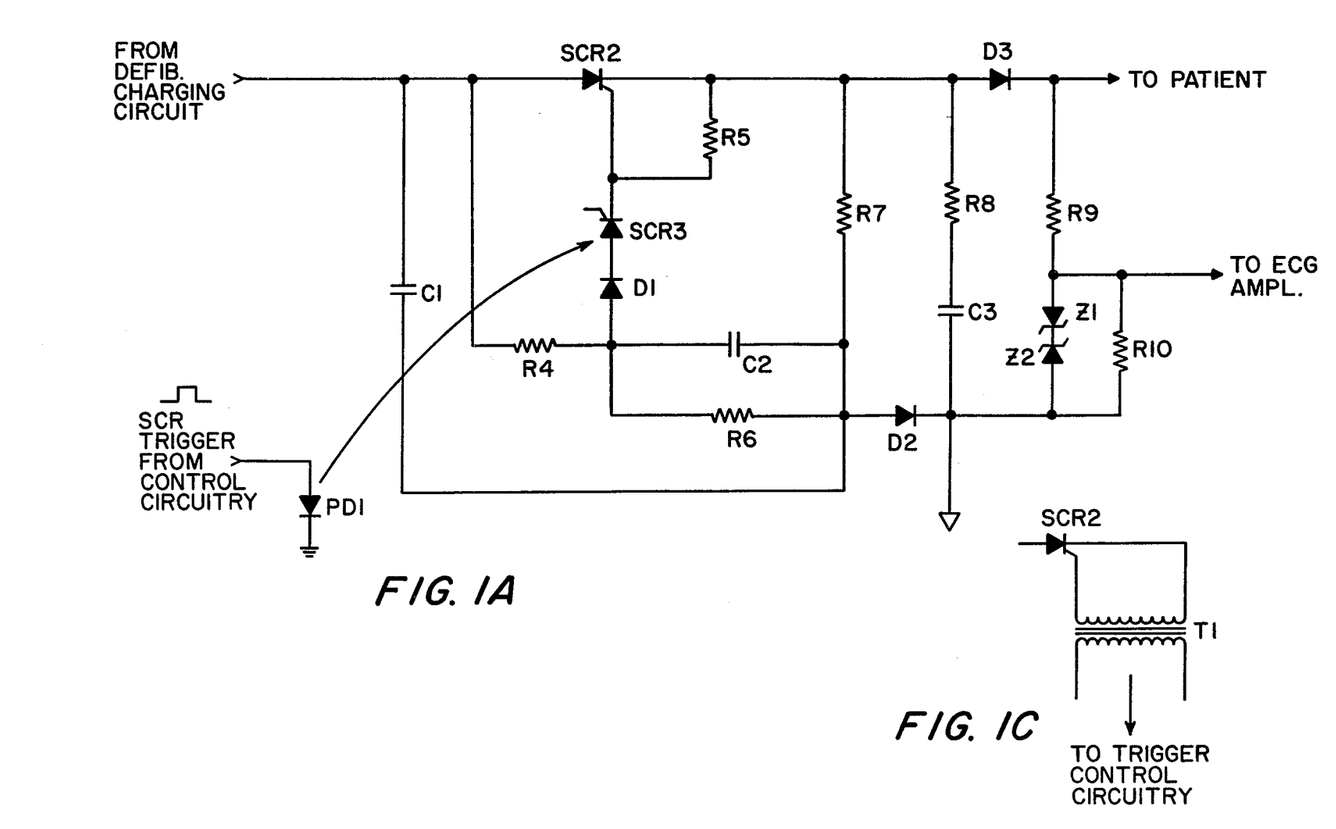
FIGS. 1A, 1B, and 1C are schematic representations of two embodiments of the present invention, as employed in an implanted defibrillator system.

Referring to FIG. 1A, the interface and protection circuitry 10 is shown in association with a high voltage capacitor C1 forming the discharge element of a defibrillator (not shown). Protection circuitry 10 includes the following elements: capacitor C1; a silicon-controlled rectifier SCR2 and associated resistor R5; optically controlled rectifier SCR3 connected to the gate lead of the rectifier SCR2 and activated by a further photodiode PD1 (in turn activated by the SCR trigger pulse input thereto); resistors R4, R6, R7 and capacitor C2 connected (as shown) between the input and output of rectifier SCR2, as well as to the cathode of rectifier SCR3 (via diode D1); resistor R8 and capacitor C3 connected between the output of rectifier SCR2 and ground; diode D3 connected between the output of rectifier SCR2 and the patient; and resistor R9, series-connected and oppositely oriented zener diodes Z1, Z2 and resistor R10 connected between the output of diode D3 and ground.

Interface and protection circuit 10 of FIG. 1A operates as follows. Rectifier SCR2 is controlled via its gate by the output of rectifier SCR3. Specifically, a trigger voltage (preferably, of approximately 20 volts) is built up, via voltage-dividing resistors R4 and R6, on capacitor C2, diode D6 being forward biased. The return point of the voltage divider R4, R6 is tied to circuit ground (via diode D2) to prevent the current through series resistors R4 and R6 from reaching the patient. Then, when the SCR trigger pulse from the control circuitry (not shown) is applied to the photodiode PD1, photo-controlled rectifier SCR3 is optically triggered, and the voltage built up on capacitor C2 is "dumped" onto the control lead of rectifier SCR2 through forward-biased diode D1 and rectifier SCR3, thus firing the rectifier SCR2. Application of the trigger voltage to the gate of rectifier SCR2 permits the passage of defibrillation voltage (previously built up on capacitor C1) through rectifier SCR2 and forward-biased diode D3, and the defibrillation voltage is applied to the patient.

When rectifier SCR2 is gated on in this manner, the trigger control circuitry (not shown) for controlling the rectifier SCR3 (via diode PD1) is protected by the optical isolation between the control circuitry and the high-voltage capacitor C1. Since the cathode and gate of rectifier SCR2 will rise to the capacitor voltage when rectifier SCR2 is gated, due in part to resistor R5, and since photo-SCR's typically are not capable of blocking such high voltages, diode D1 is utilized and reverse biases during the defibrillation pulse, thus protecting rectifier SCR3.

In a preferred embodiment of the present invention, the resistor R5, connected between the cathode and the gate of rectifier SCR2, is set at a resistance value so as to improve the resistance of rectifier SCR2 to false triggering, such as from dv/dt. Moreover, a low impedance return path for gate current pulses is provided by the series combination of small-value resistor R8 and capacitor C3 which, together, form a path for gate current return. In addition, resistor R7 holds the cathode of rectifier SCR2 to near ground through forward-biased diode D2, and thus serves as a return path for leakage current from the rectifier SCR2, preventing DC leakage current from reaching the patient during capacitor charging, since D3 must be forward-biased to apply current to the patient lead. Resistor R7 also serves as a pathway for the SCR holding current which is required for reliable pulsing of the defibrillation electrodes.

During application of defibrillation voltage to the patient, resistor R9 (which is set to a high resistance value) consumes the high voltage (approximately 800 volts), so that the ECG amplifier (not shown) connected to the junction between resistor R9 and zener diodes Z1 and Z2 "sees" only a very small voltage (for example, 0.6 volts). Moreover, the large value of resistor R9 does not affect the ECG amplifier since the latter typically has a high input impedance value (usually in the megohm range).

Diode D3 serves the function of partially protecting the pulse generating system when external defibrillation is applied to the patient. More specifically, when external defibrillation is applied with such a polarity that the leads from the patient "pull in" a positive voltage, diode D3 reverse-biases, and protection of the pulse generation system is thus provided in addition to the reverse-bias capability of rectifier SCR2 in combination with diode D1 (which reverse biases should rectifier SCR2 also become reverse-biased).

Moreover, diode D3 prevents the ECG amplifier from being "loaded down" by the defibrillator circuitry. Specifically, diode D3 keeps resistor R7 from being seen by the ECG amplifier, by acting like a very high resistance switch until forward-biased to about 0.5 volts. ECG potentials are insufficient to provide this forward bias of diode D3, such ECG potentials being in the millivolt range. Resistor R7, it is to be noted, is large (in the kilohm range) but is small insofar as the input impedance of the ECG amplifier is concerned (the latter being in the megohm range), and could load the ECG source (the heart leads) were it not for diode D3.

Figures 1B, 4:
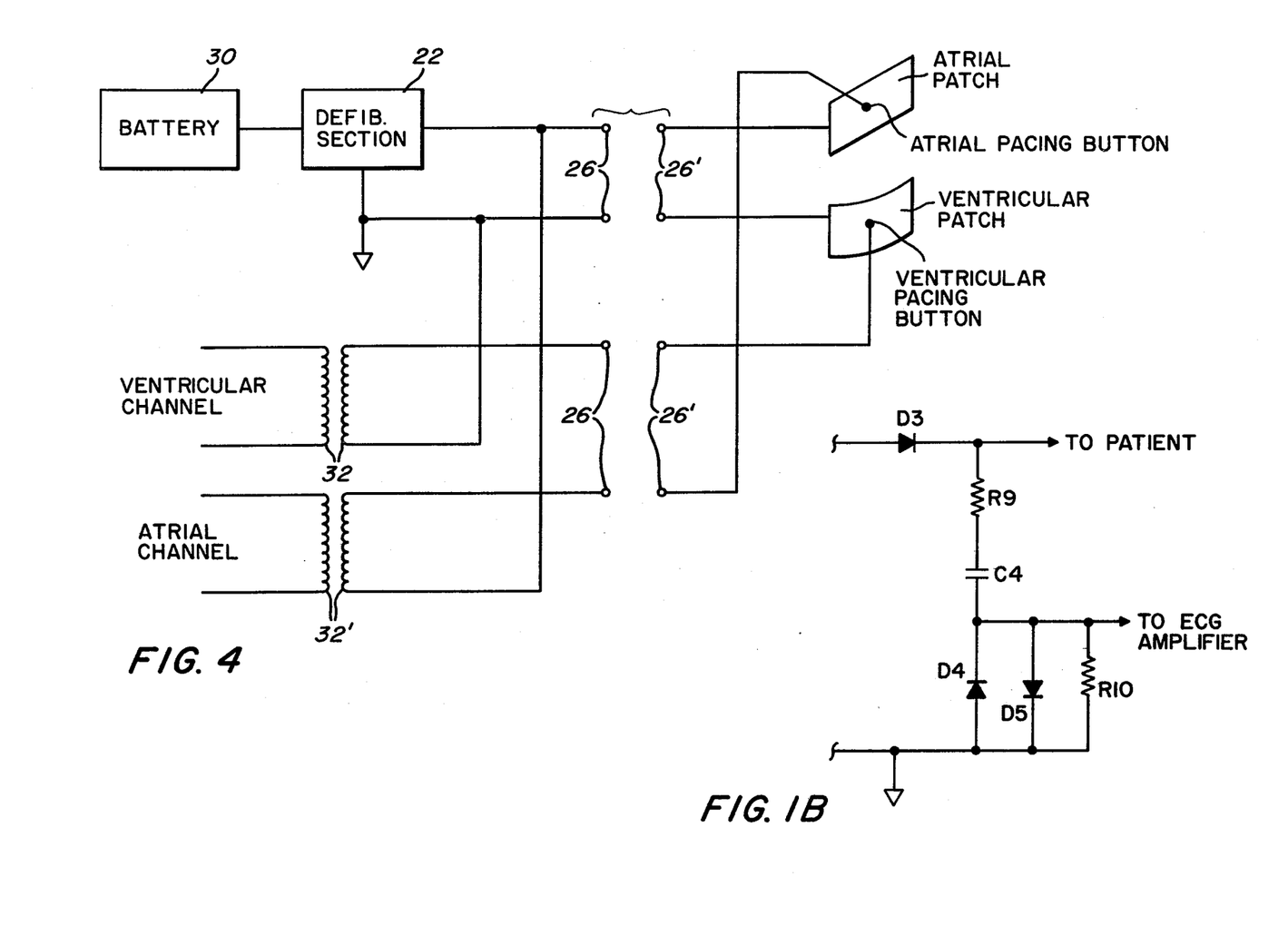
FIG. 4 is a schematic representing a further embodiment of the present invention, comprising a combination of the features of the various embodiments of FIGS. 1 through 3.

Thus, as seen in FIG. 1A, the series-connected and oppositely oriented zener diodes Z1 and Z2 will allow no more than a specified number of volts (for example, 30 volts) to be applied to the ECG amplifier, thus protecting the ECG amplifier from over-voltage during periods of defibrillation. Referring to FIG. 1B, a further embodiment of the invention calls for the provision of back-to-back diodes D4 and D5 connected in parallel arrangement between resistor R9 and ground. However, in such an arrangement, during periods of defibrillation, it was discovered that diodes D4 and D5 would become forward-biased, causing a voltage-divider effect to take place. This resulted in a diminished ECG signal. Accordingly, a blocking capacitor C4 is provided between resistor R9 and the diodes D4, D5 in order to block the DC voltage, thus preventing forward-biasing of the diodes D4, D5.

In any event, the parallel arrangement of diodes D4, D5 provides further isolation and protection for the ECG amplifier by presenting only 0.6 v. (diode drop) to the ECG amplifier during the delivery of a defibrillation pulse. These diodes are also effectively out of the circuit (they present a very high impedance) with respect to the ECG signals for the same reasons as stated for diode D3.

It is to be recognized that the embodiments of FIGS. 1A and 1B can be combined for further protection. That is to say, series-connected and oppositely oriented zener diodes Z1, Z2 can be combined in parallel with parallel-connected diodes D4, D5, with a blocking capacitor C4 being provided between the resistor R9 and the parallel combination.

The defibrillator circuitry is protected against negative-going induced pulses by the forward-bias blocking action of rectifier SCR2. Should an external defibrillation pulse be applied with such a polarity that the patient lead is pulsed negative, diode D3 would be forward-biased, applying the negative potential to the protection cathode and gate of rectifier SCR2. The same negative potential appears at the anode of diode D2, which reverse-biases. The time constant of resistors R4, R6 and capacitor C2 is chosen such that rectifier SCR3 can block any potential built up on its anode, thus preventing rectifier SCR2 from being gated and keeping it in its forward-biased blocking mode.

It is to be noted that the silicon-controlled rectifier SCR2 employed in the circuit of FIG. 1A typically may have a "breakdown" voltage of 800 volts. Thus, it is considered quite preferable to employ an arrangement comprising two series-connected circuits 10, as disclosed in FIG. 1A and as described above. As a result, a total of 1600 volts would be needed to "break down" the silicon-controlled rectifiers, thus adding an additional safety feature.

Finally, it should be recognized that it is possible to achieve isolation between the trigger control circuitry (not shown) and the silicon-controlled rectifier SCR2 of the circuit 10 of FIG. 1A in another way. Whereas optical isolation is employed, in the embodiment shown in FIG. 1A, utilizing photodiode PD1 in conjunction with optically controlled rectifier SCR3 (and associated resistors R4, R6 and capacitor C2), it is also possible to utilize transformer-type isolation by replacing the aforementioned elements by a transformer T1 shown in FIG. 1C of the present application. The disadvantage of transformer isolation is that transformers having the required primary-to-secondary voltage breakdown tend to be quite large, whereas, with modern hybrid techniques, the circuit of FIG. 1A (though more complex) may be smaller and more reliable.

Figure 2:
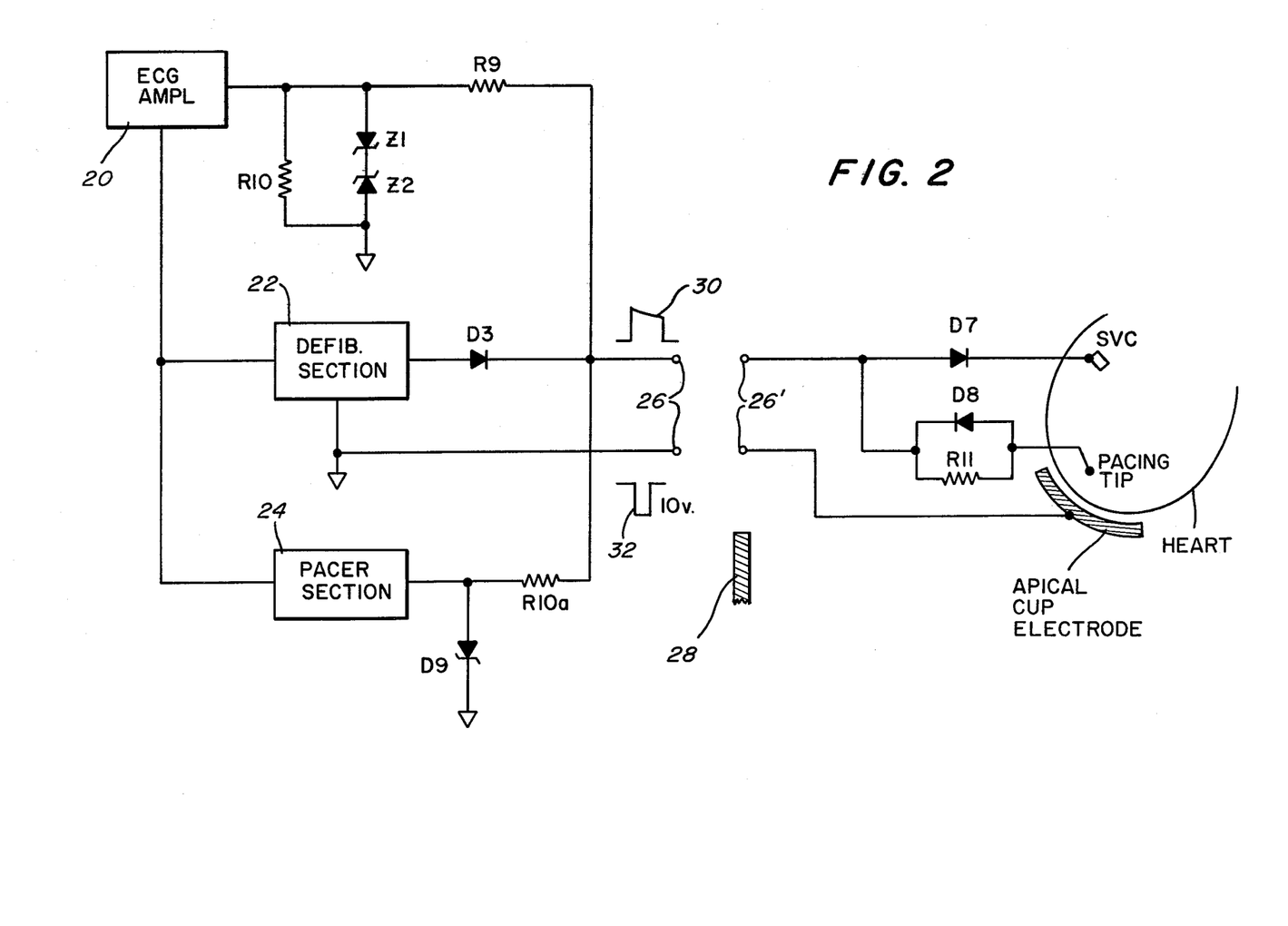
FIG. 2 is a schematic representation of a further embodiment of the present invention, as employed in a combined defibrillator-pacer system.

FIG. 2 is a further embodiment of the present invention, as implemented in a combined defibrillator-pacer system, with the advantage that defibrillator pulses and pacing pulses are transmitted over the same lead pair while eliminating an implantable connector.

As shown therein, the arrangement comprises an ECG amplifier 20, a defibrillator section 22 and a pacer section 24 connected to output electrode terminals 26. Resistors R9 and R10, capacitor C4 and zener diodes Z1 and Z2, appearing at the output of ECG amplifier 20, are the same as the identically referenced elements in FIG. 1A. The latter elements protect the ECG amplifier 20 in the manner previously described with respect to FIG. 1A.

Referring back to FIG. 1A, the remaining elements (to the left of diode D3) of the interface and protection circuitry 10 are contained within the defibrillator section 22 of FIG. 2. However, the arrangement of FIG. 2 includes additional circuit elements, as follows: resistor R10a is connected to the output of pacer section 24, and zener diode D9 connects the junction between pacer section 24 and resistor R10 to ground.

Terminals 26 at the output of defibrillator section 22 and pacer section 24 communicate with corresponding electrode leads 26' associated with the patient's heart. These are the connections which must be passed into the defibrillator case 28. Two leads, as compared to three (which would be required in a conventional circuit), are employed. Connections into the case 28 are difficult to make, and ability to minimize them is an advantage.

A first one of the electrode connections 26—26', communicates with a superior vena cava electrode SVC via diode D7, and further communicates with a pacing tip (typically, located within the right ventricle of the heart) via the parallel arrangement of diode D8 and resistor R11. Elements D7, D8 and R11 are external to the defibrillator case 28, and must be included in the heart leads, and this allows the novel multiplexing of pacer pulses and defibrillation pulses over the same leads to be carried out in accordance with the present invention. It is the possibility of including electronic components within the heart lead assembly which results in this advantage.

A second one of the electrode connections 26—26' communicates with an apical cup electrode in contact with the apex of the heart. It is further to be noted that, in the arrangement of FIG. 2, the defibrillator can or case 28 "floats." The defibrillator output (see waveform 30 in FIG. 2) travels through diode D3 and diode D7 to the superior vena cave electrode SVC, through the heart to the apical cup electrode, with a return path being provided via the lowermost electrode lead 26' to ground. The negative pacer output pulse (see waveform 32) travels via resistor R10a (diode D9 being reverse-biased) and the parallel combination of resistor R11 and forward-biased diode D8 to the pacing tip, through the heart to the cup electrode, with a return path being provided via the lowermost electrode lead 26' to ground. It is to be noted that this arrangement provides the preferred cathodal stimulation pulses to the pacing tip.

More specifically, during defibrillation, defibrillator section 22 provides output 30 via diodes D3 and D7. The ECG amplifier 20 is protected from the defibrillation output as previously described, while resistor R10a and diode D9, which is forward-biased by the positive defibrillation pulse, provide protection for the pacer section 24 by dropping the defibrillator voltage across resistor R10a. The defibrillator output forward biases diode D7, permitting current to flow from the superior vena cava electrode SVC to the apical cup electrode, thus defibrillating the heart. The pacing tip is protected from defibrillator current by means of diode D8, which reverse-biases, and by means of resistor R11, which has a high enough impedance so as to limit the defibrillation current appearing at the pacing tip to a safe level. Diode D8, by maintaining a reverse-biased status, blocks the majority of the defibrillation current and prevents it from reaching the pacing tip.

During the operation of pacer 24, a pacer output pulse 32 (which is negative in polarity relative to ground) is provided to electrode lead 26 via resistor R10a, the resistance of resistor R10a being low enough for the pacer pulse (normally from a current source) to flow to the electrode lead 26 without much loss in pacer voltage. The pacer output is further provided to diode D7 which reverse-biases, effectively removing the superior vena cava electrode SVC from the circuit and preventing pacer current from flowing into the electrode SVC. Moreover, diode D8 forward-biases, permitting pacing current to flow to the pacing tip. Ihe apical cup electrode is maintained at ground and, therefore, pacing current travels through the heart from the pacing tip to the apical cup electrode, with a return path being provided via the lowermost electrode lead 26' to ground. To prevent electrode corrosion during pacing, pacer output circuits are typically AC-coupled by a capacitor, ensuring no net DC current flow in the leads. Resistor R11 is included to provide a return current path for the output-coupling capacitor of the pacer, thus minimizing electrode corrosion.

During the provision of a pacer pulse 32 by the pacer section 24, zener diode D9 does not break down, and thus the pacer pulse 32 is, as just described, provided to the heart via resistor R10a. However, when an external defibrillating pulse is applied, zener diode D9 does break down, and the external defibrillating pulse is clamped by the diode D9, providing pacer protection.

The sensing operation performed by ECG amplifier 20 proceeds as follows. As mentioned previously, the diode D3 prevents the defibrillator output from loading the ECG amplifier 20. Diode D7 effectively isolates the electrode SVC from the ECG amplifier 20. Since the pacer section 24 is a current source, loading of the ECG amplifier 20 by the pacer section 24 is not a problem. Moreover, the resistors R9 and R11 are small relative to the input impedance of the ECG amplifier 20. As a result, the ECG signals are relatively uninhibited during sensing.

Thus, ECG signals are received by ECG amplifier 20 via resistors R9 and R11, the measured ECG signals representing voltage between the pacing tip and cup electrode on the heart.

Again, the above description has been rendered in connection with an arrangement (of FIG. 2) wherein the defibrillator can or case 28 is "floating." In a defibrillator, the case cannot be connected to either of the defibrillating leads or else current will flow into the case, decreasing defibrillator efficacy. Battery supply ground is in common with one of the defibrillator leads, and conventional pacers provide pacer pulses with respect to battery ground. Thus, either the case must float, or isolation of pacer pulses must be provided.

Figures 3A, 3B:
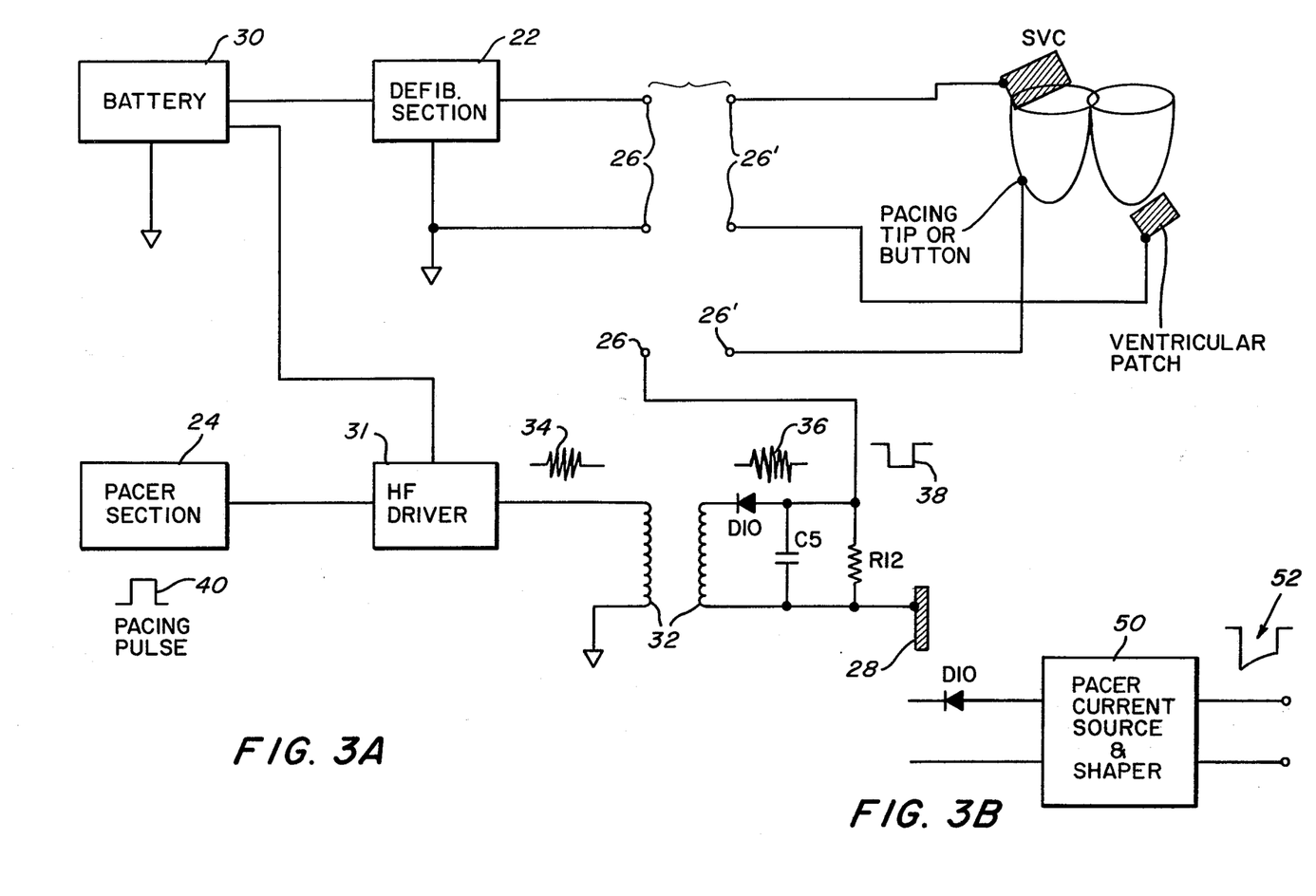
FIGS. 3A and 3B are schematic representations of a further embodiment of the present invention, as employed in a combined defibrillator-pacer system.

FIG. 3A is a further embodiment of the present invention as employed in a combined defibrillator-pacer arrangement utilizing isolation of pacer pulses. In this arrangement, the defibrillator section 22 is shown connected to battery 30 for the provision of power thereto, defibrillator section 22 also being connected via terminals 26 and electrode lead connections 26' to a superior vena cava patch electrode SVC and a ventricular patch electrode, respectively. The pacer section 24 is shown connected via a high frequency driver 31 to the primary of a transformer 32, the secondary of the transformer 32 being connected, via a diode D10 and a connector pin combination 26—26', to a pacing tip or button. It is to be noted that, in this case, three connections are required to exit the defibrillator can or case, since the components (in the previous embodiment) which allow pulse multiplexing have been omitted for clarity. A parallel arrangement of capacitor C5 and resistor R12 is connected between the anode of diode D10 and the defibrillator case 28. One side of the primary winding of transformer 32 is grounded, as shown, while the corresponding side of the secondary winding of transformer 32 is connected to the can 28. Thus, the can 28 and the components in the secondary of transformer 32 "float" with respect to battery ground.

The transformer 32 is a high frequency transformer which easily passes a high frequency signal, such as that provided by high frequency driver 31 in response to application of pacer pulses from the pacer section 24. More specifically, pacer section 24 emits a pulse 40 which controls HF driver 31, the latter emitting a high frequency burst signal having a duration equal to that of the pulse 40. Thus, the input signal (pulse waveform 40) is modulated in the primaty winding of transformer 32 by driver 31, and is subsequently demodulated in the secondary circuit (secondary winding plus elements D10, C5 and R12) of transformer 32, resulting in recovery of the pulse input 40 on the demodulator side. That is to say, the output 36 of transformer 32 is demodulated by diode D10, in conjunction with the parallel arrangement of capacitor C5 and resistor R12, to develop the envelope 38 of the waveform 36. This signal is an inverted version of the original pacing pulse 40, and is applied to the pacing tip or button located in association with the heart.

A further embodiment of the present invention results from variation of the embodixent of FIG. 3A, as indicated in FIG. 3B. Therein, resistor R12 (FIG. 3A) has been replaced by pacer current source and shaper circuit 50. The circuit 50 produces, in a manner which would be obvious to one of skill in the art, a specifically shaped pacer pulse 52, which is more suitable for application to the heart of the patient through the pacing tip or button.

Defibrillator 22, as powered by battery 30, provides defibrillator pulses via terminals 26 and electrode lead connections 26' across the superior vena cava patch electrode SVC and ventricular patbh electrode, as shown in FIG. 3, and as previously described with respect to FIGS. 1 and 2.

The primary purpose of providing transformer 32 in the arrangement of FIG. 3A is to permit the pacing circuit to use the defibrillator case 28 as a return path while isolating the case 28 from the defibrillator pulsing circuit. Some defibrillation current will flow through the case 28, but any such current must also flow through the pacer lead and does not reduce defibrillation efficiency. Furthermore, any such current is minimized by abdominal placement of the defibrillator package, and by placing the pacing tip near the ventricular patch, thus minimizing any potential difference between the pacing button and the case 28, caused by defibrillator pulse fringe fields.

Additionally, a further advantage is obtained by employing the modulation-demodulation technique with the transformer. Specifically, employment of signal modulation (in transformer 32 by driver 31) and demodulation (in the secondary of transformer 32 and elements D10, C5 and R12) permits a reduction in the size of transformer 32, with resultant advantages in terms of reduced size and cost.

FIG. 4 is a schematic representing a further embodiment of the present invention, comprising a combination of the features of the various embodiments of FIGS. 1A, 1B, 2 and 3. The arrangement in FIG. 4 comprises a battery 30 in combination with a defibrillator section 22, terminals 26 and electrode lead connections 26'. It is to be noted that, whereas the respective embodiments of FIG. 2 and FIGS. 3A, 3B disclose two pairs and three pairs, respectively, of terminals in electrode lead connections, the embodiment of FIG. 4 includes four pairs of terminals 26 and electrode lead connections 26'. The first two electrode lead connections 26' are connected to the atrial and ventricular patches, respectively, the third electrode lead connection 26' being connected to a ventricular pacing button, and the fourth electrode lead connection 26' being connecting to an atrial pacing button.

The terminals 26 corresponding to the latter two electrode lead connections 26' are connected, via transformers 32 and 32', respectively, to ventricular and atrial channels, respectively. Thus, the embodiment of FIG. 4 performs the following three functions.

Defibrillator section 22, connected to battery 30, provides defibrillation pulses via the first two pairs of terminals 26 and electrode lead connections 26' to the atrial and ventricular patches, respectively, thus accomplishing defibrillation of the patient.

The ventricular pacing channel of FIG. 4 is connected to conventional pacer circuitry, such as pacer section 24 of FIGS. 2 and 3A, 3B (discussed above), so that a pacing pulse can be applied, via transformer 32 and the third and second pairs, respectively, of terminals 26 and lead connections 26', to the patient; that is, the ventricular pacing pulses are applied between the ventricular pacing button and the ventricular patch.

Finally, the atrial pacing channel is connected to conventional pacer circuitry so that atrial pacing pulses can be applied, via transformer 32' and the fourth and first pairs, respectively, of terminals 26 and electrode lead connections 26', to the patient; that is, the pacing pulses are applied between the atrial pacing button and the atrial patch.

It is to be recognized that, whereas FIG. 4 shows only transformers 32 and 32', the arrangement can be augmented by inclusion of HF driver 31, diode D10, capacitor C5 and resistor R12, so as to employ modulation and demodulation, as described above relative to FIG. 3A.

While preferred forms and arrangements have been shown in illustrating the invention, it is to be clearly understood that various changes in detail and arragement may be made without departing from the spirit and scope of this disclosure.

We claim:

1. An implantable defibrillation system for implantation in a patient comprising a ground reference, defibrillating means for generating high-voltage defibrillating pulses, an ECG amplifier for sensing cardiac signals, common conductor means electrically connected to both said defibrillating means and said ECG amplifier for transferring both defibrillating pulses and cardiac signals respectively to and from said patient through said ground reference, said defibrillating means being connected to said common conductor means, and interface means being electrically connected to said amplifier and said common conductor means for limiting the voltage applied to said amplifier during the presence of a defibrillating pulse and for transferring a substantial portion of said cardiac signal to said amplifier during the absence of a defibrillating pulse.

2. The system of claim 1, wherein said interface means includes impedance means and at least one pair of series-connected, oppositely poled diode means connected in series between said common conductor means and said reference thereby to form an impedance-diode network, said network being responsive to said defibrillating pulse to produce thereacross a substantial portion of the voltage appearing on said conductor means during the presence of a defibrillating pulse while simultaneously minimizing the voltage applied to said amplifier; and during the absence of a defibrillating pulse, said network being responsive to receive thereacross a substantial portion of the voltage signal appearing on said conductor means and to provide said voltage signal to said amplifier.

3. The system of claim 1, wherein said interface means includes impedance means connected in series with at least one pair of oppositely poled, parallel-connected diode means, said impedance means and diode means being connected between said common conductor means and said ground reference, said impedance means being responsive to said defibrillating pulse to produce thereacross a substantial portion of the voltage appearing on said conductor means during the presence of a defibrillating pulse while simultaneously minimizing the voltage applied to said amplifier, and during the absence of a defibrillating pulse, said diode means being responsive to receive thereacross a substantial portion of the voltage signal appearing on said conductor means and to provide said voltage to said amplifier.

4. The system of claim 3, wherein said interface means further comprises isolation means interposed between said common conductor means and said ECG amplifier for isolating said ECG amplifier from DC voltage.

5. The system of claim 1, further comprising triggering means for providing trigger pulses and a trigger circuit connected to said defibrillator being responsive to said trigger pulses for passing said defibrillation pulses over said common conductor means to said patient.

6. The system of claim 5, wherein said trigger circuit comprises a rectifier having a control lead, said rectifier being actuated by said trigger pulses to pass said defibrillation pulses.

7. The system of claim 6, wherein said rectifier is an optically controlled rectifier, and further includes a photodiode connected to said triggering means responsive to said trigger pulses for activating said optically controlled rectifier, said optically controlled rectifier being responsive thereto for activating said rectifier via said control lead thereof to pass said defibrillation pulses.

8. The system of claim 2 wherein said diode reans comprise zener diodes.

9. An implantable defibrillation system for implantation in a patient comprising a ground reference, a defibrillator for generating high-voltage defibrillating pulses, an ECG amplifier for sensing cardiac signals, common conductor means electrically connected to both said defibrillating means and said ECG amplifier for transferring both defibrillating pulses and cardiac signals respectively to and from said patient through said ground reference, said amplifier means being connected to said common conductor means for receiving said cardiac signals, and defibrillator interface means being electrically connected to said defibrillator and said common conductor means for prevention said defibrillator from loading said ECG amplifier while said defibrillation system is implanted in said patient.

10. The system of claim 9, wherein said prevention means comprises a resistor connected between said defibrillator and said ground reference, said connection of said resistor to said defibrillator forming a junction, said defibrillation interface means further comprising a diode connected between said junction and said ECG amplifier.

11. The system of claim 9, further comprising triggering means for providing trigger pulses and a trigger circuit connected to said defibrillator being responsive to said trigger pulses for passing said defibrillation pulses over said common conductor means to said patient.

12. The system of claim 11, wherein said trigger circuit comprises a rectifier having a control lead, said rectifier being actuated by said trigger pulses to pass said defibrillation pulses.

13. The system of claim 12, wherein said rectifier is an optically controlled rectifier, and a photodiode connected to said triggering means is responsive to said trigger pulses for activating said optically controlled rectifier, said optically controlled rectifier being responsive thereto for activating said rectifier via said control lead thereof to pass said defibrillation pulses.

14. An implantable defibrillation system for implantation in a patient comprising a ground reference, a defibrillator for generating defibrillating pulses, an ECG amplifier for sensing cardiac signals, common conductor means electrically connected to both said defibrillating means and said ECG amplifier for transferring both defibrillating pulses and cardiac signals respectively to and from said patient through said ground reference, said amplifier means being connected to said conductor means, for receiving cardiac signals, and defibrillator protection means being electrically connected to said defibrillator and said common conductor means for protecting said defibrillator from externally applied defibrillating pulses applied to said patient while said implantable defibrillation system is implanted in said patient.

15. The system of claim 14, wherein said protection means comprises a diode connected between said defibrillator and said patient.

16. The system of claim 14, further comprising triggering means for providing trigger pulses and a trigger circuit connected to said defibrillator being responsive to said trigger pulses for passing said defibrillation pulses over said common conductor means to said patient.

17. The system of claim 16, wherein said trigger circuit comprises a rectifier having a control lead, said rectifier being actuated by said trigger pulses to pass said defibrillation pulses.

18. The system of claim 17, wherein said defibrillator protection means further includes an optically controlled rectifier, and a photodiode connected to said triggering means and responsive to said trigger pulses for activating said optically controlled rectifier, said optically controlled rectifier being responsive thereto for activating said rectifier via said control lead thereof to pass said defibrillation pulses.

19. A combined defibrillator-pacer system for implantation in a patient and for selectively defibrillating and pacing the patient, said system comprising a ground reference, defibrillator means for generating high-voltage defibrillation pulses, a pacer connected, in parallel with said defibrillator means for generating pacing pulses, an electrocardiograph (ECG) amplifier for sensing cardiac signals and being connected in parallel with said defibrillator means and said pacer, common conductor means electrically connected to both said defibrillating means and said ECG amplifier for transferring both defibrillating pulses and cardiac signals respectively to and from said patient through said ground reference, said defibrillating means being connected to said common conductor means, and interface means being electrically connected to said amplifier and said common conductor means for limiting the voltage applied to said amplifier during the presence of a defibrillating pulse and for transferring a substantial portion of said cardiac signal to said amplifier durinq the absence of a defibrillating pulse.

20. The system of claim 19, wherein said interface means include impedance means and at least one pair of series-connected, oppositely poled diode means connected in series between said common conductor means and said ground reference thereby to form an impedance-diode network, said network being responsive to said defibrillating pulse to produce thereacross a substantial portion of the voltage appearing on said conductor means during the presence of a defibrillating pulse while simultaneously minimizing the voltage applied to said amplifier, and durinq the absence of a defibrillating pulse, said network being responsive to receive thereacross a substantial portion of the voltage signal appearing on said conductor means and to provide said voltage signal to said amplifier.

21. The system in claim 19, wherein said interface means includes impedance means connected in series with at least one pair of oppositely poled, parallel-connected diode means, said impedance means and diode means being connected between said common conductor means and said ground reference, said impedance means being responsive to said defibrillating pulse to produce thereacross a substantial portion of the voltage appearing on said conductor means during the presence of a defibrillating pulse while simultaneously minimizing the voltage applied to said amplifier, and during the absence of a defibrillating pulse, said diode means being responsive to receive thereacross a substantial portion of the voltage signal appearing on said conductor means and to provide said voltage to said amplifier.

22. The system of claim 21, wherein said interface means further comprises isolating means interposed between said common conductor means and said ECG amplifier for isolating said ECG amplifier from DC voltage.

23. The system of claim 19, wherein said patient is equipped with first and second electrodes and a pacing tip, said system further comprising first connection means for connecting said defibrillator means, said pacer, and said ECG amplifier to said first electrode and said pacing tip, and second connection means for connecting said second electrode to said electrical ground.

24. The system in claim 23, wherein said first connection means comprises a forward-biased diode to permit defibrillation of said patient.

25. The system in claim 23, wherein said first connection means comprises a parallel resistor-diode arrangement for permitting pacing of said patient, said arrangement for including a reverse-biased diode and a resistor of high impedance for protecting said pacing tip from said defibrillation pulses.

26. The system in claim 19, further comprising triggering means for providing trigger pulses, said interface means including a trigger circuit connected to said defibrillator means and responsive to said trigger pulses for passing said defibrillation pulses over said common conductor means to said patient.

27. The system in claim 26, wherein said trigger circuit comprises a rectifier having a control lead, said rectifier being actuated by said trigger pulses to pass said defibrillation pulses.

28. The system in claim 26, wherein said interface means further includes an optically controlled rectifier, and a photodiode connected to said triggering means and responsive to said trigger pulses for activating said optically controlled rectifier, said optically controlled rectifier being responsive thereto for activating said rectifier via said control lead thereof to pass said defibrillation pulses.

29. A combined defibrillator-pacer system for implantation in a patient and for selectively defibrillating and pacing the patient, said system comprising a ground reference, defibrillator means for generating high-voltage defibrillation pulses, a pacer connected in parallel with said defibrillator means for generating pacing pulses, an electrocardiograph (ECG) amplifier for sensing cardiac signals and being connected in parallel with said defibrillator means and said pacer, common conductor means electrically connected to both said defibrillator means and said ECG amplifier for transferring both defibrillating pulses and cardiac signals respectively to and from said patient through said ground reference, said amplifier means being connected to said common conductor means for receiving said cardiac signals, and defibrillator interface means being electrically connected to said defibrillator means and said common conductor means for preventing said defibrillator means from loading said ECG amplifier while said defibrillation system is implanted in said patient.

30. The system of claim 29, wherein said interface means comprises a resistor connected between said defibrillator means and said electrical ground, said connection of said resistor to said defibrillator means forming a junction, said interface means further comprising a diode connected between said junction and said ECG amplifier.

31. The system of claim 30, wherein said interface means further comprises a tunnel diode connected between said junction and said diode.

32. The system of claim 29, wherein said patient is equipped with first and second electrodes and a pacing tip, said system further comprising first connection means for connecting said defibrillator means, said pacer, and said ECG amplifier to said first electrode and said pacing tip, and second connection means for connecting said second electrode to said electrical ground.

33. The system of claim 32, wherein said first connection means comprises a forward-biased diode to permit defibrillation of said patient.

34. The system of claim 32, wherein said first connection means comprises a parallel resistor-diode arrangement for permitting pacing of said patient, said arrangement including a reverse-biased diode and a resistor of high impedance for protecting said pacing tip from said defibrillation pulses.

35. The system of claim 29, further comprising triggering means for providing trigger pulses, said interface means including a trigger circuit connected to said defibrillator and responsive to said trigger pulses for passing said defibrillation pulses to said patient over said common conductor means.

36. The system of claim 35, wherein said trigger circuit comprises a rectifier having a control lead, said rectifier being actuated by said trigger pulses to pass said defibrillation pulses.

37. The system of claim 36, wherein said interface means further includes an optically controlled rectifier, and a photodiode connected to said providing means and responsive to said trigger pulses for activating said optically controlled rectifier, said optically controlled rectifier being responsive thereto for activating said rectifier via said control lead thereof to pass said defibrillation pulses.

38. A combined defibrillator-pacer system for implantation in a patient and for selectively defibrillating and pacing a patient, said system comprising a ground reference, defibrillator means for generating defibrillation pulses, a pacer connected in parallel with said defibrillator for generating pacing pulses, an electrocardiograph (ECG) amplifier for sensing cardiac signals and being connected in parallel with said defibrillator and said pacer, common conductor means electrically connected to both said defibrillating means and said ECG amplifier for transferring both defibrillating pulses and cardiac signals respectively to and from said patient through said ground reference, said amplifier means being connected to said conductor means for receiving cardiac signal, and defibrillator protection means being electrically connected to said defibrillator means and said common conductor means for protecting said defibrillator means from externally applied defibrillating pulses applied to said patient while said implantable defibrillation system is implanted in said patient.

39. The system in claim 38, wherein said protection means comprises a diode connected between said defibrillator means and said patient.

40. The system in claim 38, wherein said patient is equipped with first and second electrodes and a pacing tip, said system further comprising first connection means for connecting said defibrillator means said pacer, and said ECG amplifier to said first electrode and said pacing tip, and second connection means for connecting said second electrode to said electrical ground.

41. The system of claim 40, wherein said first connection means comprises a forward-biased diode to permit defibrillation of said patient.

42. The system of claim 41, wherein said first connection means comprises a parallel resistor-diode arrangement for permitting pacing of said patient, said arrangement including a reverse-biased diode and a resistor of high impedance for protecting said pacing tip from said defibrillation pulses.

43. The system of claim 38, further comprising triggering means for providing trigger pulses, said protection means including a trigger circuit connected to said defibrillator means and responsive to said trigger pulses for passing said defibrillation pulses to said patient over said common conductor means.

44. The system of claim 43, wherein said trigger circuit comprises a rectifier having a control lead, said rectifier being actuated by said trigger pulses to pass said defibrillation pulses.

45. The system of claim 44, wherein said protection means further includes an optically controlled rectifier, and a phtodiode connected to said providing means and responsive to said trigger pulses for activating said optically controlled rectifier, said optically controlled rectifier being responsive thereto for activating said rectifier via said control lead thereof to pass said defibrillation pulses.

* * * * *